US 9,072,454 B2
Jul. 7, 2015

(12) United States Patent
Irion et al.

(54) LIGHT SOURCE DEVICE FOR ENDOSCOPIC OR EXOSCOPIC APPLICATIONS

(75) Inventors: Klaus-Martin Irion, Emmingen-Liptingen (DE); Thomas Hinding, Aldingen (DE); Werner Goebel, Singen (DE)

(73) Assignee: KARL STORZ GMBH & CO. KG (DE)

( * ) Notice: Subject to any disclaimer, the term of this patent is extended or adjusted under 35 U.S.C. 154(b) by 928 days.

(21) Appl. No.: 13/074,975

(22) Filed: Mar. 29, 2011

(65) Prior Publication Data

US 2011/0235324 A1    Sep. 29, 2011

(30) Foreign Application Priority Data

Mar. 29, 2010   (DE) .......................... 10 2010 013 307

(51) Int. Cl.
   *A61B 1/06*   (2006.01)
   *A61B 1/07*   (2006.01)
   *A61B 1/04*   (2006.01)

(52) U.S. Cl.
   CPC ................. *A61B 1/07* (2013.01); *A61B 1/0676* (2013.01); *A61B 1/0661* (2013.01); *A61B 1/0638* (2013.01);
   (Continued)

(58) Field of Classification Search
   CPC .. A61B 1/0638; A61B 1/0684; A61B 5/0084; A61B 1/0669; A61B 1/0653; A61B 1/05; A61B 1/07; A61B 1/00009; A61B 1/00096; A61B 1/0676; A61B 1/0661; A61B 5/0075; A61B 1/005; A61B 1/0125; A61B 18/1477; G02B 6/0006; G02B 6/4296; F21K 9/56; A61N 5/0603; G01N 2021/6419; G01N 2201/0627; A61K 49/006; A61L 2202/10; A61L 2202/24; A61L 2/10; A61L 2/26; A61M 2025/0161; A61M 2025/1047; A61M 2025/105; A61M 25/0026; A61M 25/0147; A61M 25/0152; A61M 25/0158; A61M 25/09; A61M 25/1002; A61M 25/1011; A61M 29/02; A61M 31/002; A61M 37/0092; A61M 39/1011; A61M 39/16; A61M 39/20
   USPC .......... 362/574, 231, 277, 555, 551; 600/178, 600/476, 180, 104, 160, 339, 113, 117, 600/200; 348/68, 45; 607/89, 92; 382/162
   See application file for complete search history.

(56) References Cited

U.S. PATENT DOCUMENTS

| 2002/0087205 A1* | 7/2002 | Chen ............................. 607/88 |
| 2008/0077200 A1* | 3/2008 | Bendett et al. ................. 607/89 |

(Continued)

FOREIGN PATENT DOCUMENTS

| DE | 20018213 U1 | 12/2000 |
| DE | 10141559 A1 | 3/2002 |

(Continued)

OTHER PUBLICATIONS

European Search Report; Application No. EP 11 15 9313; Issued: Sep. 5, 2011; 8 pages.

(Continued)

*Primary Examiner* — Stephen F Husar
*Assistant Examiner* — Danielle Allen
(74) *Attorney, Agent, or Firm* — Whitmyer IP Group LLC

(57) ABSTRACT

A light source device for endoscopic or exoscopic applications includes a flat first light source, a second light source, an illuminating beam path that is configured to provide a first light beam emanating from the first light source for an endoscopic or exoscopic application, and a coupling device to couple a second light beam from the second light source into the illuminating beam path, whereby the coupling device is configured in such a way that at the coupling site the cross-section surface of the second light beam is smaller than the cross-section surface of the first light beam.

16 Claims, 6 Drawing Sheets

(52) U.S. Cl.
CPC ............. *A61B 1/0669* (2013.01); *A61B 1/0684* (2013.01); *A61B 1/043* (2013.01); *A61B 1/063* (2013.01); *A61B 1/0653* (2013.01)

(56) References Cited

U.S. PATENT DOCUMENTS

2009/0021739 A1   1/2009   Tsujita et al.
2009/0040754 A1   2/2009   Brukilacchio et al.

FOREIGN PATENT DOCUMENTS

| | | |
|---|---|---|
| DE | 10305599 A1 | 8/2004 |
| DE | 202005006497 U1 | 9/2005 |
| DE | 102006005528 A1 | 8/2006 |
| DE | 102007015492 A1 | 7/2008 |
| EP | 1279364 A2 | 1/2003 |
| EP | 2020202 A2 | 2/2009 |
| WO | 0175359 A1 | 10/2001 |
| WO | 2004070844 A1 | 8/2004 |

OTHER PUBLICATIONS

German Search Report; Application No. 102010013307.8; Dec. 27, 2010; 4 pages.

* cited by examiner

LIGHT SOURCE DEVICE FOR ENDOSCOPIC OR EXOSCOPIC APPLICATIONS

CROSS-REFERENCE TO RELATED APPLICATIONS

The present application claims priority of German patent application No. 10 2010 013 307.8 filed on Mar. 29, 2010, the content of which is incorporated herein by reference.

FIELD OF THE INVENTION

The present invention relates to a light source device with at least two light sources for endoscopic or exoscopic applications.

BACKGROUND OF THE INVENTION

To generate light to illuminate an object that is to be observed by an endoscope, tungsten halogen lamps and especially gas discharge lamps are primarily used, for example xenon-short arc lamps, other halide short arc lamps and high-pressure mercury vapor lamps. These light sources are customarily combined in a light source device with their own power source, a control or regulation filter and a blower for discharging waste heat. The light source device is produced as a separate unit from its own endoscope and is connected with the proximal end of the endoscope by a light conductor cable.

Disadvantages of the aforementioned light sources concern the degree of effectiveness or power requirement and waste heat, dimension and modular capacity. An attractive alternative concerning these aspects consists in light diodes, in particular inorganic semiconductor light diodes, and increasingly also organic light diodes. A disadvantage of a light diode, in comparison to a conventional light source, consists in the fact that not only the radiant flux Phi generated by it, but also the specific irradiance R (in $Wm^{-2}$) and the emittance $B=d^2Phi/dA\ d\ Omicron\ cos(0)$ (in $Wm^{-2}$ steradians$^{-1}$) are smaller or definitely smaller than with conventional light sources. The radiant power also that can be coupled into the light conductor cable to transmit the illuminating light to the endoscope has therefore been smaller heretofore.

Light from a conventional light source, because of the high achievable radiant capacity and intensity, can be filtered to generate, for instance, excitation light for autofluorescence or for fluorescence of protoporphyrin IX induced by 5-aminolevulinic acid (ALA) previously administered to a patient or for fluorescence of indocyanine green. The excitation filter being used is as a rule transparent only in a narrow wavelength range, in order to avoid over-radiation of the weak fluorescent light by remitted excitation light.

If a conventional light source is replaced by a white light diode, there remains after a corresponding filtering only a low radiant capacity in the desired narrow range of the excitation light, because of the aforementioned disadvantages of the light diode. This low radiant capacity typically no longer suffices to achieve sufficient illumination in the desired object distances or to sufficiently illuminate large hollow spaces. What is desired is therefore a light source device in which a spectrum generated by the light source device is feasible not subtractively by removing a filter, but additively by mixing or combining light from several light sources.

SUMMARY OF THE INVENTION

An object of the present invention consists in providing a light source device with a first light source and a second light source for endoscopic or exoscopic applications.

This object is achieved through the content of the independent claims.

Refinements are described in the dependent claims.

A light source device for endoscopic or exoscopic applications includes a flat first light source, a second light source, an illuminating beam path that is configured to provide a first light beam emanating from the first light source for an endoscopic or exoscopic application, and a coupling device to couple a second light beam from the second light source into the illuminating beam path, whereby the coupling device is configured in such a way that at the coupling site the cross-section of the second light beam is smaller than the cross-section of the first light beam.

The flat first light source is, in particular, flat to the extent that it comprises a level or essentially level light-emitting surface. Thus the first light source is distinguished, for example, from many conventional tungsten lamps and gas discharge lamps. Its bulbs, as a rule, are at least approximately cylindrical or rotationally elliptical, or in particular spherical. The coiled filaments themselves are helical structures with strongly curved surfaces. In a gas discharge lamp the area in which the gas discharge takes place is not sharply delineated, but in any case it is not level as a rule. An example of a flat light source with a particularly level light-emitting surface is an inorganic or organic light diode or an array of light diodes.

In contrast to the first light source, the second light source is in particular pointed or essentially pointed in configuration. This is true in immediate comparison with a flat light source such as a light diode, for example for many lasers, whose beam cross-section at the decoupling mirror can be very small.

The second light source can be positioned in the same unit or structural group or in the same apparatus as the first light source. Alternatively the second light source is positioned in a separate unit or a separate apparatus. The light source device can be configured as separate from an endoscope and as a unit that can be connected by a light conductor cable. In this case the illuminating beam path in particular includes the light conductor cable. The illuminating beam path, alternatively or in addition to a light conductor cable, can include one or more additional optical elements, for example a light conductor body, a diffuser, a coupling for detachable mechanical and optical coupling to a light conductor cable, lenses, mirrors, prisms, grids and other optical elements.

The optional light conductor body includes in particular a transparent or partly transparent material. With an opaque material, the light conductor body can act simultaneously as a diffuser. The optional light conductor body can be provided as a taper or in other ways with a means to focus or reduce the cross-section of the illuminating beam path.

Alternatively the light source device is partly or completely integrated into an endoscope. Both the first light source and the second light source can be positioned either on the proximal end or on the distal end of the endoscope. If the first light source is positioned on the proximal end of an endoscope, the illuminating beam path includes for example a lightwave conductor or a bundle of lightwave conductors that optically couple the first light source with a light outlet window on the distal end of the endoscope.

If the first light source is positioned on the distal end of an endoscope, the illuminating beam path includes, for example, only a light outlet window of a transparent material, which closes the distal end of the endoscope insulating it against fluids, and in some cases a spatial area in the endoscope at its distal end between the first light source and the light outlet window. If the first light source is positioned on the distal end of an endoscope and the second light source is positioned on the proximal end of the endoscope or is coupled with it by means of a light conductor cable, the coupling device includes, for example, one or more lightwave conductors, which extend from the proximal end of the endoscope to its distal end.

The light source device can be configured to provide illuminating light with any desired predetermined spectrum or several alternative predetermined or discretely or continuously modifiable spectra. For example, the light source device can be configured for alternative provision of illuminating light with a spectrum perceived as white by the human eye and with illuminating light with one or more alternative excitation spectra, which are suited to excite fluorescence.

"Light" here designates in particular electromagnetic radiance within the spectral range visible to the human eye, but in addition also electromagnetic radiance in the neighboring spectral ranges, in particular in the ultraviolet and infrared ranges.

The spectra perceived as white by the human eye are those that comprise no gaps or other imbalances, or no major ones, and with which a color temperature between 2500 Kelvin and 6500 Kelvin can be associated. Light is perceived as especially pure white if it has a color temperature between 3500 and 6500 Kelvin, and even more if it has a color temperature between 4500 and 6500 Kelvin.

The light source device can alternatively or additionally be configured to provide illuminating light for an endoscopic application for providing illuminating light for an exoscopic application.

An exoscope is an apparatus intended and configured for use outside the body for visual inspection or observation of objects in medicine, in particular objects on or close to external surfaces of a human or animal body. Unlike an endoscope, an exoscope is not configured to be inserted into a natural or artificial cavity through a small natural or artificial opening. An exoscope is instead configured for observing an object that, at least during the observation, in particular during an operation, is visible from outside. Accordingly, the exoscope is found during its intended use partly or completely outside the human or animal body and, unlike the endoscope, does not necessarily comprise a long, thin shaft.

An exoscope can be configured to include one or more video cameras or light-sensitive image sensors for two-dimensional or three-dimensional recording and display, for example on a screen. Alternatively, an exoscope can be configured as monocular or binocular for direct observation with the human eye. An exoscope is as a rule configured or optimized for an object distance in the range of a few or fewer centimeters or a few decimeters. An exoscope can have a strong enlargement device, which allows a resolution that is not achievable with the naked eye, and thus can comprise properties of a magnifying glass or stereo magnifying glass or of a microscope or stereo microscope. The exoscope is distinguished from the microscope or stereo microscope as a rule by a larger object distance.

The coupling site is the location from which in the light downstream direction the second light beam runs in the illuminating beam path and essentially in the same direction as the first light beam. As is described in more detail hereafter, the coupling site is constituted, for example, by one end of a lightwave conductor, from which the second light beam emerges, by a lens or an aperture through which the second light beam enters the illuminating beam path, or by a mirror or a grid by means of which the second light beam is diverted in the direction of the first light beam. The coupling site is therefore as a rule a small area or a level or curved surface, in particular a borderline surface or a surface on the end of a lightwave conductor or a surface of a lens or mirror.

The cross-section surfaces of the first light beam and of the second light beam are in particular cross-sections along a plane perpendicular to the main propagation direction of the particular light beam, which includes or intersects the coupling site. Both the cross-section surface of the first light beam and the cross-section surface of the second light beam are connected at the coupling site, in particular simply or multiply connected. A cross-section surface is simply connected if each loop within the cross-section surface can be pulled together to a point. A cross-section surface is multiply connected or n-connected, if, in simplified terms, it includes one or more holes. Alternatively, however, both the cross-section surface of the first light beam and the cross-section surface of the second light beam can each be non-connected or can consist of several connected surfaces isolated from one another.

Edges of cross-section surfaces are formed, for example, by diaphragms or by edges of mirrors, lenses, prisms, or grids, by surfaces of lightwave conductors or the edge of a mantle surface of a lightwave conductor on its end. At sites where the cross-section of a light beam is not sharply outlined, the edge of the cross-section is defined, for example, by the number of points at which the intensity is 50% or another predetermined fraction of the maximum intensity.

In a light source device as described here, at the coupling site the cross-section surface of the second light beam is smaller, in particular essentially smaller, than the cross-section surface of the first light beam. At the coupling site, the cross-section surface of the second light wave is in particular at most half, a fifth, a tenth, a twentieth, a fiftieth or hundredth of the cross-section surface of the first light beam. Corresponding dimensions apply to the contents of the light-emitting surfaces of the light sources. The content of the light-emitting surface of the second light source is in particular smaller or essentially smaller than the content of the light-emitting surface of the first light source, so that the proportion, for example, is at most 1:2, 1:5, 1:10, 1:20, 1:50 or 1:100.

The light source device described here makes possible, for example, a combination of two light sources with different radiation characteristics, in particular with different size of the light-emitting surface and/or with different divergence of the emitted light, and a simultaneous or alternating coupling of their light into the same illuminating beam path. For example, the light of a light diode or of an array of light diodes with a relatively large light-emitting surface can be united or mixed or combined with the light of a laser diode or another diode laser, which can be bundled onto a very small surface and can be coupled with minor losses into a lightwave conductor.

The light source device makes possible in addition an alternating coupling of light from the first light source and light from the second light source into the illuminating beam path without being forced to optically modify the beam path. Therefore, light from the first and from the second light sources can be alternatingly coupled very quickly. This makes possible, for example with endoscopic or exoscopic investigations, an illumination that varies from image to image, for example an alternating illumination with a white light spectrum and an excitation spectrum for exciting fluorescence.

Unlike with a unification of two light beams by means of a dichroic mirror or by means of a polarization-dependent reflecting mirror, a low-loss combination of the light from two light sources is also possible when they differ from one another neither in wavelength nor in polarization. For example, the light from a broad-band emitting light diode can be combined with the light of a laser with a wavelength that lies within the emission spectrum of the broad-band emitting light diode. This makes possible, for example, a modification of the spectrum generated by the light diode by addition of the light of a laser.

The coupling device includes in particular a lightwave conductor with a first end and a second end, where the first end of the lightwave conductor is coupled with the second light source and where the second end of the lightwave conductor is positioned alongside, in or before the light-emitting surface of the first light source.

The lightwave conductor is, for example, a single-mode lightwave conductor, a multi-mode lightwave conductor, or a liquid lightwave conductor. The coupling device can include a single lightwave conductor of this type or several lightwave conductors of this type in the form of an ordered or unordered bundle. The first end of the lightwave conductor can be merely optically coupled, or else mechanically combined, with the second light source. If the first end of the lightwave conductor is mechanically combined with the remote light source, it can be combined with the light source so that it is separable either nondestructively or destructively.

The second end of the lightwave conductor, more precisely the light outlet surface on the second end of the lightwave conductor, is in particular the aforementioned coupling site. The light-emitting surface of the first light source is in particular level or essentially level or curved, in particular concave in curvature. The light-emitting surface of the first light source can be simply or multiply connected or not connected. Examples described more fully below are a single light diode, a single light diode with a through-hole or a hole and an array of light diodes. The coupling site lies in the light-emitting surface or in a level or minimally curved surface that contains the light-emitting surface of the first light source.

If the second end of the lightwave conductor is positioned close to the light-emitting surface of the first light source, it is in particular contiguously positioned immediately beside the light-emitting surface or on the edge of the light-emitting surface. Here the distance of the center of the second end of the lightwave conductor from the edge of the light-emitting surface of the first light source is in particular not greater than the radius or not greater than the diameter or not greater than twice the diameter of the lightwave conductor, possibly including a cladding and possibly including a coating or buffer. The second end of the lightwave conductor can be positioned on a straight or concave portion of the external edge of the light source, in particular in an indentation or notch in the external edge of the first light source.

If the second end of the lightwave conductor is positioned in the light-emitting surface of the first light source, it is in particular positioned in a through-hole or a hole in the multiply connected light-emitting surface or on a concave portion of the edge of the light-emitting surface.

At the coupling site, the light-emitting surface of the first light source is typically greater or essentially greater than the cross-section surface of the through-hole. The ratio between the light-emitting surface of the first light source and the cross-section surface of the through-hole is, for example, at least 2:1, 5:1, 10:1, 20:1, 50:1, or 100:1. For example, the light-emitting surface of the light diode is square or rectangular with a lateral length between 1 mm and 3 mm, in particular with a lateral length of approx. 2 mm. The through-hole can have a diameter of 100 micrometers or less, in individual cases even of several hundred micrometers. The light-emitting surface is thus at least about 100 times larger than the cross-section surface of the through-hole.

If the second end of the lightwave conductor is positioned before the light-emitting surface of the first light source, it is positioned downstream of the light-emitting surface in the light flux.

An advantage of using a lightwave conductor to couple the second light beam emanating from the second light source into the illuminating beam path consists in the fact that the lightwave conductor with its small cross-section requires only a small opening in the light-emitting surface of the first light source, or shadows light from the first light source only to a small extent, or makes possible a coupling of the light from the second light source directly on the edge of the light-emitting surface of the first light source. If the light from the second light source can be coupled at low loss into the lightwave conductor, the light source device makes possible an efficient combination of the light from the first light source and of the light from the second light source.

In each of the three aforementioned arrangements of the second end of the lightwave conductor near, in or before the light-emitting surface of the first light source, the second end of the lightwave conductor is in particular positioned parallel or essentially parallel to the surface normal of the light-emitting surface of the first light source. Alternatively or simultaneously, the second end of the lightwave conductor is aligned to the center of an optical element that lies opposite to, and downstream in the light flux from, the light-emitting surface of the first light source. For example, the second end of the lightwave conductor is aligned to the center of a mirror, a lens or a light inlet surface of a light conductor cable.

In a light source device as described here, the first light source includes in particular a semiconductor light source with an array of light diodes or an array of other light-emitting elements, and the coupling site is positioned between light diodes or other light-emitting elements of the array.

If the coupling device as described above includes a lightwave conductor, the second end of the lightwave conductor in particular is positioned between light diodes or other light-emitting elements of the array. Otherwise, for example, a lens, a grid or a mirror is provided to bundle light from the second light source onto a site between light diodes or other light-emitting elements of the array, in particular to a through-hole in a substrate of the array.

Light diodes of the array are in particular white light diodes, which emit light with a spectrum that is perceived as white by the human eye. For this purpose the array of light diodes includes, for example, one or more blue or violet light-emitting semiconductor junctions and a phosphorescent or fluorescent material, which partly absorbs the blue or violet light and emits green, yellow and/or red light. Alternatively the array includes light diodes that emit light with different spectra, so that altogether a white color impression arises. For example, the array can include light diodes that emit blue and yellow light, or light diodes that emit blue, green and red light.

Light diodes in an array comprise as a rule a small distance on both sides, which for example is determined by manufacturing technology and/or is required for conductor tracks. Such an intermediate space between light diodes of an array can easily suffice in order to position the end of the lightwave conductor there. A conventional array of light diodes, under certain circumstances, must only be supplemented by an aperture.

In an alternative model of the light source device, the first light source includes a light diode with an aperture, and the coupling site is positioned in the aperture.

The light diode can be a white light diode, as described above. The aperture extends in particular from the rear of the light diode to its light-emitting surface, for example in the form of an etched or bored passageway or through-hole. The aperture is in particular positioned in the center of the light-emitting surface of the light diode. The light diode is configured in such a way that no electrical dysfunction, in particular no short-circuit, occurs because of the through-hole. The aperture can be small in proportion to the light-emitting surface of the light diode, in particular reducing the light-emitting surface of the light diode only by a few percent, at most 10 percent or at most 20 percent. This is particularly true when the light from the second light source is bundled in the aperture by means of a lens, mirror, grid or other optical device. An especially small aperture is sufficient if the coupling device includes a lightwave conductor whose second end is positioned in the opening. The side of the aperture facing the light-emitting surface of the light diode, or the second end of the lightwave conductor, forms the coupling site.

In a light source device as described here, the coupling device can include at least either an object lens, a curved mirror, an optical grid or another imaging device that reduces the cross-section of the second light beam. An object lens includes one or more lenses and/or lens sets and/or one or more curved mirrors, and works in particular by combining.

The imaging device can be configured and positioned in order to generate an indentation, a tightening or a narrowing of the second light beam on the edge of the light-emitting surface of the first light source or in an opening in the light-emitting surface of the first light source or in the illuminating beam path before the light-emitting surface of the first light source. In particular, the imaging device can generate an indentation at the coupling site.

Such an indentation or narrowing of the second light beam at the coupling site makes possible an especially small disturbance of the illuminating beam path, in particular an especially small reduction of the light-emitting surface of the first light source or an especially minor shadowing of the light from the first light source.

In a light source device as described here, the coupling device can include a deflection mirror that is positioned in the illuminating beam path before the light-emitting surface of the first light source. The deflection mirror is in particular positioned downstream in the light flux ahead of the light-emitting surface of the first light source. The deflection mirror or its reflecting surface forms the coupling site from which the second light beam runs in the illuminating beam path and essentially in the same direction as the first light beam.

The deflection mirror is smaller or essentially smaller than the cross-section of the first light beam at the site of the deflection mirror in order to shadow the smallest possible portion of the first light beam. For example, the surface of the deflection mirror projected on a plane perpendicular to the main propagation direction of the first light beam is at most one-tenth, one-fifth, or half of the cross-section surface of the first light beam at the site of the deflection mirror. The cross-section surface of the first light beam here is in particular measured in a plane that is perpendicular to the main propagation direction of the first light beam and that contains the centerpoint, in particular the centroid of the surface, of the deflection mirror.

To reduce further the shadowing effect of the deflection mirror, the deflection mirror can be dichroic. The wavelength-dependencies of the reflectance and of the transmission capacity are here in particular selected in such a way that light of the second light beam is primarily reflected and light of the first light beam is primarily transmitted.

The light source device can in particular include an imaging device, which as described above generates an indentation of the second light beam, and can include the deflection mirror described above. In this case the imaging device and the deflection mirror are in particular configured and positioned so that the imaging device generates the indentation of the second light beam at the site or close to the site of the deflection mirror. In this case the deflection mirror can be especially small.

The described deflection mirror can be embedded in a light conductor body. In particular, the deflection mirror can be moulded into the light conductor body or generated in the light conductor body. Instead of a deflection mirror, it is also possible, for example, to provide a grid, which reflects wavelength-selective light of the second light beam. Such a grid, for example, after production of a light conductor body, can also be generated in said body.

In a light source device as described here, the illuminating beam path can include several first lightwave conductors whose first ends are coupled with the first light source, and the coupling device can include at least a second lightwave conductor whose first end is coupled with the second light source, so that second ends of the first lightwave conductors and second ends of the at least one second lightwave conductor are positioned parallel and close to one another on a surface.

The surface on which the second ends of the first lightwave conductors and of the at least one second light wave conductor are positioned, can be level or curved and in particular forms the coupling site of the second light beam into the illuminating beam path. If the first lightwave conductors and the at least one second lightwave conductor are already positioned parallel and close to one another a distance upstream in the light flux from the surface, the coupling site is the place from which the first lightwave conductors and the at least one second lightwave conductor are positioned close and parallel to one another.

A light source device with the illuminating beam path that includes several first lightwave conductors and at least one second lightwave conductor, is an example in which the cross-section surface of the first light beam includes several non-connecting individual surfaces, namely the cross-section surfaces of the individual light-conducting cores of the lightwave conductors. In the case of several second lightwave conductors, the cross-section surface of the second light beam is also non-connecting and includes the cross-section surfaces of the light-conducting cores of the second lightwave conductors.

An advantage of an illuminating beam path with several first lightwave conductors and at least one second lightwave conductor consists in the fact that these lightwave conductors can simultaneously be a component of a light conductor cable from the separate light source device to the proximal end of the endoscope and/or from the proximal end to the distal end of the endoscope.

In the case of several second lightwave conductors, they can be positioned randomly or quasi-randomly or regularly. The second lightwave conductors are in particular positioned corresponding to a one- or two-dimensional point grid. Thereby the light of the second light beam can be distributed in nearly any desired manner in the cross-section of the illuminating beam path.

In a light source device as described here, the first light source can be configured to generate a first spectrum with a first half-width, and the second light source to generate a second spectrum with a second half-width, so that the second half-width is no more than half of the first half-width.

The first light source is in particular configured to generate a broad spectrum in the spectral range visible to the human eye and/or in the bordering spectral ranges (infrared, ultraviolet). In particular, the first light source can be configured to generate a spectrum perceived as white by the human eye. If the first light source includes a semiconductor light source with one or more light diodes, each individual light diode or in some cases all light diodes together can be configured to emit a broad spectrum, in particular a white spectrum.

The second light source on the other hand can be configured to generate a narrow spectrum. This applies, for example, if the second light source includes a laser diode, a diode laser or another laser. The narrow spectrum of the second light source can likewise lie completely or partly within or outside the spectral range visible to the human eye. The narrow spectrum of the second light source can overlap completely or partly with the broad spectrum of the first light source.

The addition or mixture of the broad spectrum and narrow spectrum makes possible, for example, an alternating or simultaneous observation of an object in remitted white light and in fluorescent light. Alternatively, by mixing the first spectrum and the second spectrum, an improvement in the spectral characteristic can be achieved, for example an improvement in the color reproduction.

In a light source device as described here, the second light source can include a laser diode or another diode laser or another laser.

The laser diode can in particular be executed as a pigtail, so that the light of the laser diode is coupled into a first end of a lightwave conductor directly or by means of a lens or grid or another imaging device. The first end of the lightwave conductor can be connected with the laser diode in nondestructively separable or destructively separable manner, in particular by being cemented with it.

An advantage of the use of a laser consists in the fact that light emitted by it comprises an especially high intensity, in particular a high radiant capacity with a small cross-section. In addition the light emitted by a laser has an especially low divergence. Light from a laser can therefore be bundled especially well, for example in a small opening in a light diode or an array of light diodes or on a small deflection mirror. For the same reason, the light of a laser can be coupled into a lightwave conductor especially efficiently. A particular advantage of a pigtail laser diode consists in the efficient and robust coupling of the lightwave conductor to the laser diode.

Laser diodes, diode lasers and other lasers, in addition, emit as a rule only one or a few wavelengths. Because of this small-bandwidth spectrum, light can be coupled with it, for example, by means of a wavelength-selective reflecting mirror or a grid that is transparent outside a narrow wavelength range and that does not shadow light from the first light source. In addition, laser diodes, diode lasers and other laser can as a rule be quickly switched in and out and, for example, powered by pulsing.

In a light source device as described here, the first light source can be positioned in an endoscope or an exoscope, and the second light source can be positioned separately from the endoscope or exoscope.

The second light source in this case can be coupled with the endoscope or exoscope by a thin and highly flexible lightwave conductor. This lightwave conductor can be integrated in a cable with a power supply line to provide the first light source in the endoscope with electric current.

BRIEF DESCRIPTION OF THE DRAWINGS

Hereinafter embodiments are described in greater detail with reference to the appended drawings, which are as follows.

DETAILED DESCRIPTION OF THE INVENTION

Figure 1:
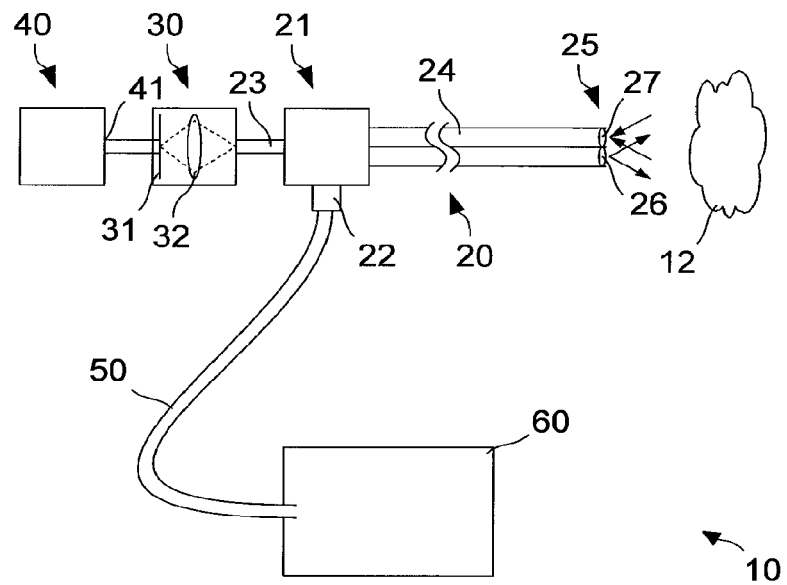
FIG. 1 shows a schematic view of an endoscopy system.

FIG. 1 shows a schematic view of an endoscopy system 10 for observing and/or optically recording an object 12. The endoscopy system 10 includes an endoscope 20. A coupling 22 for a light conductor cable and a coupling 23 for a video camera are positioned on the proximal end 21 of the endoscope 20. A rigid or flexible shaft 24 extends from the proximal end 21 to a distal end 25 of the endoscope 20. On the distal end 25 the endoscope 20 comprises a light outlet window 26 and a light inlet window 27.

The endoscope 20 is coupled with a video camera 30 by the coupling 23. The video camera 30 includes a light-sensitive image sensor 31 and an object lens 32. Contrary to the depiction in FIG. 1 and alternatively to it, instead of the video camera 30, an eyepiece can be provided through which an image of the object 12 recorded by the endoscope 20 can be observed directly by the human eye.

The proximal end 21 of the endoscope 20 is coupled with a light source device 60 by means of a light conductor cable 50 via the coupling 22. The light source device 60 is configured with one or more predetermined or modifiable illuminating spectra to generate illuminating light. Different variants of the light source device 60 are described below with reference to FIGS. 2 through 13.

Contrary to the depiction in FIG. 1 and alternatively to it, the components of the endoscopy system 10 can be partly or completely integrated. For example, the video camera control device 40 or parts thereof can be integrated into the video camera 30. The video camera 30 or the camera 30 and camera control device 40 can be integrated in the endoscope 20, for example at its proximal end 21. The light source device 60 can be integrated partly or wholly in the endoscope 20, in particular at its proximal end and/or at its distal end.

For endoscopic recording of the object 12 by means of the endoscopy system 10, the light source device 60 generates light that is coupled into the light conductor cable 50 and from it is transmitted to the proximal end 21 of the endoscope 20. Illuminating light generated by the light source device 60 is transmitted from the proximal end 21 of the endoscope 20 to its distal end 25 by means of a beam path not shown in FIG. 1, in particular by means of one or more lightwave conductors. The illuminating light emerges from the endoscope 20 at the light outlet window 26 and impinges on the object 12. The illuminating light can be absorbed, reflected, or dispersed by the object 12. In addition, the illuminating light can cause fluorescence, depending on its spectral properties and the properties of the surface of the object 12.

Reflected or dispersed illuminating light or fluorescent light emanating from the object 12 impinges on the light inlet window 27 at the distal end 25 of the endoscope 20. By means of an observation beam path not shown in FIG. 1, this light is transmitted from the distal end 25 of the endoscope 20 to its proximal end 21 and further to the video camera 30 or to an eyepiece not shown in FIG. 1. The observation beam path includes, for example, a rod lens system or an ordered bundle of light wave conductors. If a video camera is used as shown in FIG. 1, an object lens 32, which includes at least a lens, a curved mirror or another imaging device, generates a true image on the light-sensitive image sensor 31 of the video camera 30.

Embodiments of the light source device 60 are described below with reference to FIGS. 2 through 13. A housing or bordering of the light source device 60 is depicted in each case here by a broken line. The light source device 60 can include additional components in particular when it forms a unit as is indicated by the broken line. Additional components include for example a power supply to provide light sources and other components of the light source device 60 with power, in particular with electric power, and a control or regulating device to control light sources or other components of the light source device 60.

Light-emitting surfaces, light conductor cables, light conductor bodies and other optical elements are shown in part set off at a distance from one another to make clear that they constitute, at least originally, separately produced and/or functionally separated components. In fact, contrary to the depiction in FIGS. 2 through 13, these optical components can border on one another, in particular can have contiguous surfaces with one another, or can for example be cemented together. Consequently, for example, losses by reflections on bordering surfaces can be avoided or at least reduced.

Figure 2:
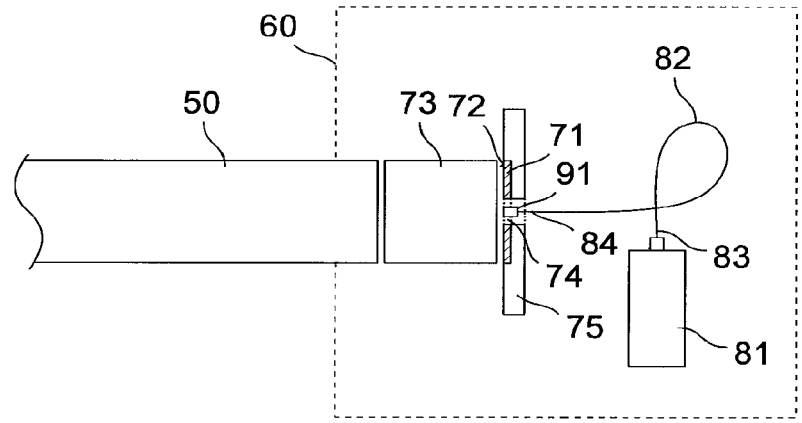
FIG. 2 shows a schematic view of a light source device.

FIG. 2 shows a light source device 60 with a light diode or an array of light diodes 71. Hereinafter it is assumed at first that the light source device 60 comprises a single light diode 71.

The light diode 71 comprises a light-emitting surface 72 that is level or essentially level. The light diode 71 can be an inorganic or organic light diode. The light diode 71 can comprise a light-emitting semiconductor junction that is configured to emit blue or violet light, and a phosphorescent or fluorescent layer on the light-emitting surface 72. The phosphorescent or fluorescent layer on the light-emitting surface 72 can be configured to absorb part of the blue or violet light and through fluorescence or phosphorescence to emit light in the green, yellow and/or red spectral range. With this structure the light diode 71 can be configured to emit light with a broad spectrum, in particular light perceived as white by the human eye. Light is perceived as white by the human eye in particular when a color temperature between 3500 and 6500 Kelvin, sometimes also even from 2500 Kelvin, is associated with it and when the color reproduction index is not too low, in particular when it is at least 50, 70 or 80.

A light conductor body 73 is positioned opposite the light-emitting surface 72 of the light diode 71. As indicated in FIG. 2, the light conductor body can be at a distance from the light-emitting surface 72 of the light diode 71. Alternatively the light conductor body 73 can have a surface contiguous with the light-emitting surface 72 of the light diode 71 or can be cemented to it. The surface of the light conductor body 73 facing the light-emitting surface 72 of the light diode 71 is a light inlet surface; the surface of the light conductor body 73 turned away from the light-emitting surface 72 of the light diode 71 is the light outlet surface. The light inlet surface and light outlet surface of the light conductor body 73 can be made non-reflecting by means of a coating, in particular when they are at a distance from the light-emitting surface 72 of the light diode or from other optical elements. Other surfaces of the light conductor body 73 can be made reflecting.

The light diode 71 comprises an opening 74 in the form of a passage hole that extends from the light-emitting surface 72 to an opposite backside of the light diode 71. The light diode 71 is positioned on a cooling body 75 that comprises an opening that corresponds with the opening 74 of the light diode 71. Because of the opening 74 the light-emitting surface 72 of the light diode 71 is not simply but multiply connected or comprises a corresponding hole.

The light source device 60 further includes a laser diode 81 and a lightwave conductor 82. A first end 83 of the lightwave conductor 82 is optically coupled with the laser diode 81, in particular cemented with the light-emitting surface of the laser diode 81. A second end 84 of the light wave conductor 82 is positioned opposite a lens 91 or, as shown in FIG. 2, touches the lens 91. The second end 84 of the lightwave conductor 82 can be cemented with the lens 91. The lens 91 is positioned in or at the opening 74 in the light diode 71. The lens 91 is, for example, a gradient index lens. The surface of the lens 91 turned away from the lightwave conductor 82 is positioned parallel to the light-emitting surface 72 of the light diode 71 and in particular lies in a plane or essentially in a plane with the light-emitting surface 72 of the light diode 71. The lens 91 makes possible a shaping of the second light beam emanating from the second end 84 of the lightwave conductor 82, in particular influencing its divergence.

One end of the light conductor cable 50 described above with reference to FIG. 1 can be positioned opposite the light outlet surface of the light conductor body 73. The light conductor body 73 or the light conductor body 73 and light conductor cable 50 together form an illuminating beam path, which is configured to provide light emanating from the light diode 71, in particular a first light beam emanating from the light diode 71, for an endoscopic or exoscopic application, in particular to illuminate an object 12 and/or to excite fluorescence on the object 12.

The dimensions of the first light beam generated by the light diode 71 and its cross-section surface are determined essentially by the light-emitting surface 72 of the light diode 71 and the cross-sections of the light conductor body 73 and in some cases of the light conductor cable 50. The main propagation direction of the first light beam generated by the light diode 71 in the illuminating beam path corresponds essentially to the surface normals of the light-emitting surface 72 of the light diode 71, the light inlet surface and the light outlet surface of the light conductor body and to the longitudinal axis or longitudinal direction of the light conductor cable 50.

Light generated by the laser diode 81 is coupled on the first end 83 into the lightwave conductor 82, transmitted from it to its second end 84 and coupled by means of the lens 91 into the light conductor body 73 and thus into the illuminating beam path. The site of coupling the second light beam generated by the laser diode 81 into the illuminating beam path is the opening 74 in the light diode 71, in particular that portion of the plane that is defined by the light-emitting surface 72 of the light diode 71 and that lies within the opening 74. In the broader sense the light outlet surface of the lens 91 or the portion of the light inlet surface of the light conductor body 73 opposite the opening 74 in the light diode 71 can be considered the coupling site.

At the coupling site the second light beam, generated by the laser diode 81 and transmitted by the lightwave conductor 82, comprises a cross-section surface that corresponds at most to the cross-section surface of the opening 74 in the light diode 71. At the same site or in the same plane, the cross-section surface of the first light bundle emanating from the light diode 71 corresponds essentially to the light-emitting surface 72 of the light diode 71. Thus the cross-section surface of the second light beam generated by the laser diode 81 is essentially smaller than the cross-section surface of the first light beam generated by the light diode 71. The main directions of the first light beam emanating from the light diode 71 and of the second light beam generated by the laser diode are equal or essentially equal from the coupling site downstream in the light flux.

If the light diode 71, as described above, is a white light diode, the laser diode 81 is configured, for example, to emit blue, violet, red or other light to excite fluorescence on the object 12. The light diode 71 and the laser diode 81 are, for example, operated in alternation to radiate the object 12 alternately with white light and with fluorescence-excitation light. Simultaneous radiation or illumination of the object 12 with white light and with fluorescence-excitation light is also possible.

Alternatively, the laser diode 81 can be configured, for example, to emit green, yellow or red light that complements the spectrum emitted by the light diode 71. For this purpose the light diode 71 and the laser diode 81 are in particular operated simultaneously. The reference to a simultaneous operation with light diode 71 and laser diode 81 also signifies an operation in which the light diode 71 and the laser diode 81 only partially emit light simultaneously or in such rapid alternation that the various illumination conditions can no longer be resolved in time by the human eye or by the video camera 30. For example, the light diode 71 and the laser diode 81 can be operated in alternation so quickly that the object 12 is illuminated once or repeatedly with light of the light diode 71 and once or repeatedly with light of the laser diode 81 within the illumination interval of a single image or half-image recorded by the video camera 30.

By supplementing the light emitted by the light diode 71 with light emitted by the laser diode 81, the spectrum of the illuminating light illuminating the object 12 can be improved to such an extent that a better color impression results, in particular a natural color impression. This occurs in particular if the color reproduction index of the spectrum of the illuminating light is increased.

As already mentioned, the light source device 60 can include, instead of a single light diode 71, an array of light diodes with one- or two-dimensional regular or irregular arrangement of light diodes. In this case the lens 91 can be positioned in an intermediate area between two light diodes, so that reference number 74 designates an intermediate area between two light diodes instead of an opening in one light diode. An array of light diodes, instead of one light diode, can also be foreseen in each of the light source devices presented hereinafter with reference to FIGS. 3 through 14.

Figure 3:
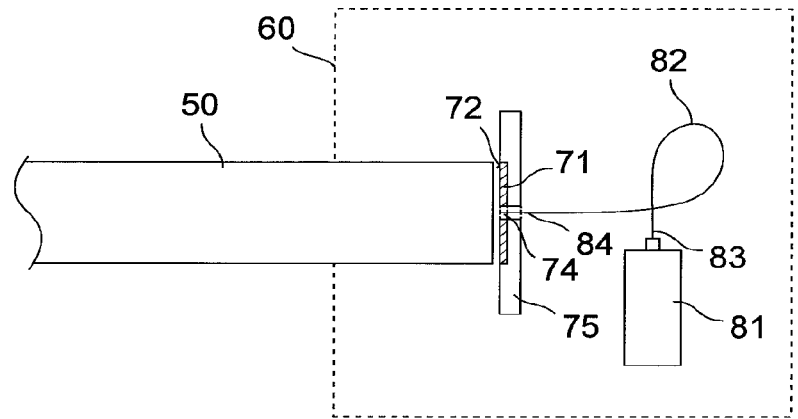
FIG. 3 shows a schematic view of an additional light source device.

FIG. 3 shows a light source device 60 similar to the light source device presented above with reference to FIG. 2. The light source device 60 is distinguished from the light source device presented above and in FIG. 2 in particular in that no light conductor body 73 is foreseen. In addition the light source device 60 comprises no lens in the opening 74 in the light diode 71. The two differences are independent of one another. This also applies for the most part to the embodiments described with reference to the other drawings. Characteristics of the embodiments can therefore be freely combined with one another to some extent, so that different advantages can be attained for different applications and to meet different conditions.

In the absence of a light conductor body, as shown in FIG. 3, the illuminating beam path is at first made up essentially of the space before the light-emitting surface 72 of the light diode 71 or, more precisely, the space into which the light diode 71 emits light of a minimum intensity. If the light conductor cable 50 is inserted in the light source device 60 or is constantly connected with it, the illuminating beam path, similarly as explained above and in FIG. 2, is bounded by the cladding surface of the light-conducting core of the lightwave conductor 50.

Dispensing with a light conductor body reduces the number of boundary surfaces at which disturbing reflections can occur and reduces production costs. The same advantages apply independently as well for dispensing with the lens 91 shown in FIG. 2 on the second end 84 of the lightwave conductor 82. By dispensing with a lens in the opening 74 of the light diode 71, the space requirement is reduced and the opening 74 in the light diode 71—contrary to what is shown in the drawings—must comprise only an insignificantly larger cross-section than the lightwave conductor 82.

Figure 4:
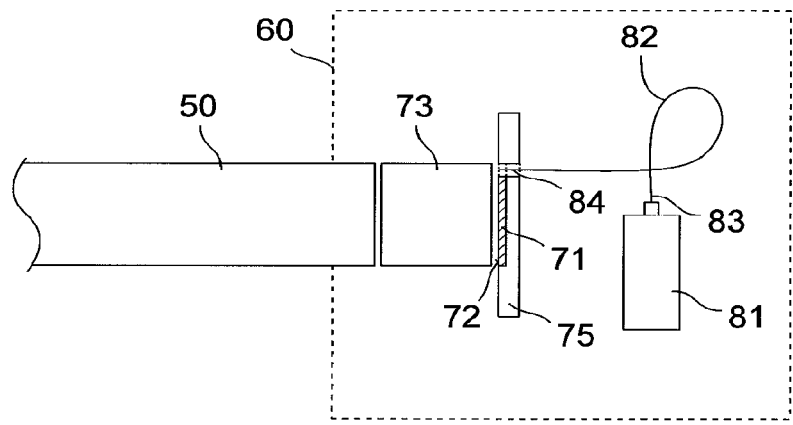
FIG. 4 shows a schematic view of an additional light source device.

FIG. 4 shows a schematic view of an additional light source device 60, which is similar in some characteristics to the light source devices described above with reference to FIGS. 2 and 3. The light source device 60 is distinguished from the one presented above and in FIG. 2 in that the second end 84 of the lightwave conductor 82 is not positioned in an opening 74 but on the edge of the light diode 71. The second end 84 of the lightwave conductor 82 can be positioned on a straight or concave portion of the outer edge of the light diode 71, in particular in an indentation or recess of the outer edge of the first light source.

The arrangement shown in FIG. 4 comes about, for example, when the light diode 71 or its light-emitting surface 72 is rectangular and the cross-section of the light conductor body 73 is circular in shape. In general the arrangement is as shown in FIG. 4 when the cross-section of the light conductor body 73 extends out beyond the light-emitting surface 72 of the light diode 71 in at least one location.

Another difference between the light source device 60 and the one presented above with respect to FIG. 2 consists in the fact that, similarly as in the light source device presented above and in FIG. 3, no lens is foreseen on the second end 84 of the lightwave conductor 82. Thus it is possible to realize the advantages described above with reference to FIG. 3.

The two aforementioned differences in the light source device 60 from the one presented in FIG. 1 are again to a great extent independent of one another. In particular, a lens can be provided even with an arrangement of the second end 84 of the lightwave conductor 82 on an outer edge of the light diode 71. The second end 84 of the lightwave conductor 82 can be positioned on the edge of the light diode 71 even with the light source device without light conductor body as presented above in FIG. 3.

An advantage of the positioning of the second end 84 of the lightwave conductor 82 on the edge of the light diode 71 consists in the fact that it is not necessary to have an opening. The production costs of the light diode 71 can therefore be lower.

Figure 5:
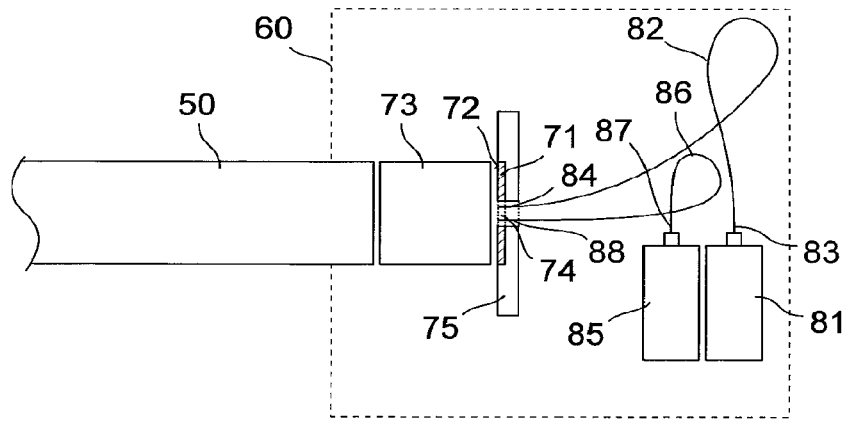
FIG. 5 shows a schematic view of an additional light source device.

FIG. 5 shows a schematic depiction of a light source device 60, which is similar in many respects to the light source device depicted above in FIG. 2. The light source device 60 is distinguished in particular from the light source device shown above in FIG. 2 in the fact that two laser diodes 81, 85 are foreseen, with two lightwave conductors 82, 86. A first end 83 of the first lightwave conductor 82 is coupled with the first laser diode 81. A first end 87 of the second lightwave conductor 86 is coupled with the second laser diode 85. Second ends 84, 88 of the two lightwave conductors 82, 86 are positioned in an opening 74 in the light diode 71. Alternatively the second ends 84, 88 of the light wave conductors 82, 86 can be positioned in two openings in the light diode 71 at a distance from one another.

The two laser diodes 81, 85 can be configured to emit light with the same spectrum or with two different spectra. If both laser diodes 81, 85 emit the same spectrum, their radiant capacity can be added together by the coupling of the light of two laser diodes. If the laser diodes 81, 85 emit light with different wavelengths, their light can be used for alternative or simultaneous excitation of different fluorescences or for improvement or correction of the spectrum generated by the light diode 71.

In the light source device 60, unlike in the light source device described above with reference to FIG. 2 and similar to the light source devices described above and in FIGS. 3 and 4, no lenses are provided on the second ends 84, 88 of the light source conductors 82, 86. This can have the advantages of lower production costs and of a lesser space requirement in the opening 74, as presented above with reference to FIGS. 3 and 4. Alternatively in the light source device 60, similarly as in the light source device presented above with reference to FIG. 2, one or two lenses can be provided on the second ends 84, 88 of the light wave conductors 82, 86.

Figure 6:
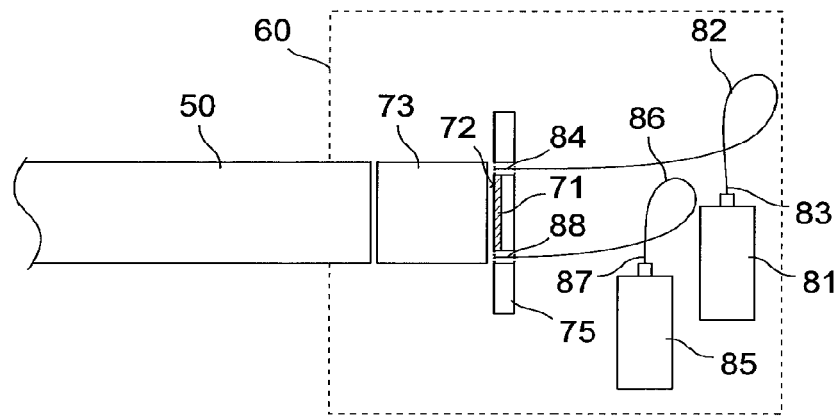
FIG. 6 shows a schematic view of an additional light source device.

FIG. 6 shows a schematic view of a light source device 60, which in several characteristics is similar to the light source devices presented above with reference to FIGS. 2 and 5. Similarly as in the light source device presented above and in FIG. 5, two laser diodes 81, 85 are equipped with two lightwave conductors 82, 86. Unlike in the light source device presented above and in FIG. 5, however, the second ends 84, 88 of the lightwave conductors 82, 86 are not positioned in an opening but rather on the edge of the light diode 71. In particular, the second ends 84, 88 of the lightwave conductors 82, 86 are positioned on opposite portions of the edge of the light diode 71. These opposite portions can be straight or curved, in particular concave.

Advantages of this arrangement and additional properties can correspond to those of the light source devices described above with reference to FIG. 4 or 5. Similarly as with the light source devices presented above and in FIGS. 3 through 5, no lenses are provided on the second ends 84, 88 of the lightwave conductors 82, 86. Contrary to the depiction in FIG. 6, but similarly as with other light source devices described above and with their variants, lenses are provided on the second ends 84, 88 of the lightwave conductors 82, 86.

In the light source devices presented above with reference to FIGS. 5 and 6, the light of a laser diode can be coupled into the illuminating beam path by means of several light wave conductors whose second ends are positioned in several different openings 74 or at various points on the edge of the light diode 71. Instead of two laser diodes 81, 85 whose light is coupled into the illuminating beam path by means of two lightwave conductors 82, 86, light from three or more laser diodes can be coupled into the illuminating beam path by a corresponding number of lightwave conductors.

The light source devices presented above with reference to FIGS. 4 through 6 each comprise a light conductor body, as already described above with reference to FIG. 2. Contrary thereto and as an alternative, the light source devices presented above with reference to FIGS. 4 through 6 can each be configured without a light conductor body. In this case the light conductor cable 50 can be optically coupled or optically coupled and mechanically connected, removably or permanently (for example, by means of an optically transparent cement), with the light-emitting surface 72 of the light diode 71 and with the second ends 84, 88 of the lightwave conductors 82, 86 or lenses positioned on them.

A light conductor body 73 can contribute to the homogenization or mixing of the light beams generated by the light diode 71 and the laser diode or laser diodes 81, 85. This applies in an arrangement of the second end or ends 84, 88 of lightwave conductors 82, 86 in openings 74 and in particular in an arrangement of the second end or ends 84, 88 on the edge of the light diode 71. For this purpose the light conductor body 73 has, for example, slightly opaque properties.

Figure 7:
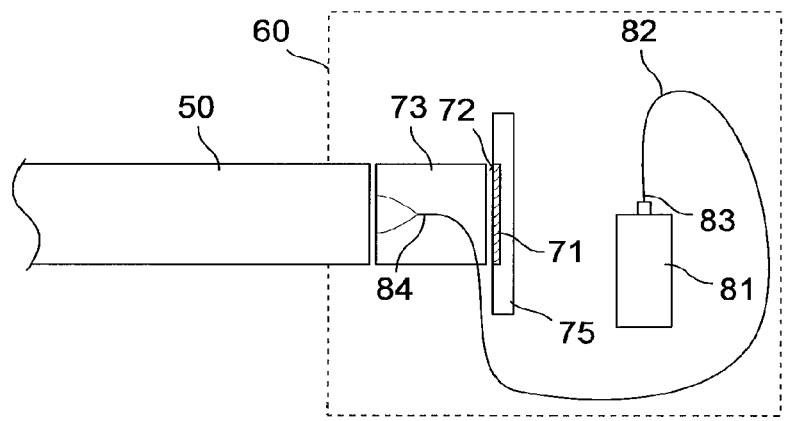
FIG. 7 shows a schematic view of an additional light source device.

FIG. 7 shows a schematic depiction of a light source device 60, which is similar in a few characteristics to the light source devices presented above in FIGS. 2 through 6. The light source device 60 is distinguished from the light source device presented above with reference to FIG. 2 in particular in the fact that the second end 84 of the lightwave conductor 82 is not positioned in an opening in the light diode 71, but rather downstream in the light flux before the light-emitting surface 72 of the light diode 71. The second end 84 of the lightwave conductor 82 for this purpose is, in particular, positioned in the light conductor body 73, for example moulded into it. The second end 84 of the lightwave conductor 82 is positioned parallel to the surface normal of the light-emitting surface 72 of the light diode 71 and thus parallel to the main radiation direction of the light diode present at this site.

In the light source device 60 the front surface on the second end 84 of the lightwave conductor 82 constitutes the coupling site of the second light beam generated by the laser diode 81 into the illuminating beam path defined on this spot essentially by the light conductor body 73. Because of the orientation of the second end 84 of the lightwave conductor 82, at the coupling site the main radiant directions of the first light beam emanating from the light diode 71 and of the second light beam generated by the laser diode 81 are equal. Contrary to the depiction in FIG. 7, on the second end 84 of the lightwave conductor 82 a small lens can be provided to form the second light beam emanating from the lightwave conductor 82 on the second end 84.

Contrary to the depiction in FIG. 7, the lightwave conductor 82 can move not laterally but rather through an opening in the light diode 71 into the light conductor body 73. In this case the arrangement is for example similar as shown above in FIGS. 2 and 5, but the second end 84 of the lightwave conductor 82 extends above the light-emitting surface 72 and protrudes into the light conductor body 73. The coupling site in this case is the front surface on the second end 84 of the lightwave conductor 82.

Figure 8:
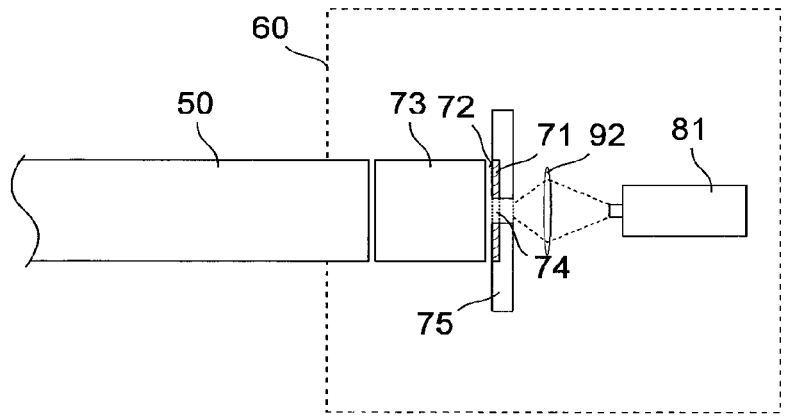
FIG. 8 shows a schematic view of an additional light source device.

FIG. 8 shows a schematic depiction of a light source device 60, which is similar in a few characteristics to the light source devices presented above with reference to FIGS. 2 through 6.

The light source device 60 is distinguished from the light source device presented above with reference to FIG. 2 in particular in that instead of a lightwave conductor, an object lens 92 is provided that in particular includes one or more lenses. The laser diode 81 and the object lens 92 are positioned in relation to the light diode 71 and the opening 74 in the light diode 71 in such a way that the second light beam generated by the laser diode 81 comprises an indentation or narrowing in the opening 74.

The coupling site of the second light beam generated by the laser diode 81 into the illuminating beam path bounded essentially by the light-emitting surface 72 and the cross-section of the light conductor body 73 is the side of the opening 74 that faces the light-emitting surface 72 of the light diode 71. If the light conductor body 73 is directly contiguous with the light-emitting surface 72 of the light diode 71, the portion of the light inlet surface of the light conductor body 73 bordering on the opening 74 is also a coupling site.

To form the second light beam generated by the laser diode 81 at the place of entry into the illuminating beam path, a lens or object lens can be provided in the opening 74, contrary to FIG. 8. Also with the light source device 60, the light conductor body can be absent—similarly as in the light source devices or their variants as presented above with reference to FIGS. 2 through 6. In this case, contrary to FIG. 8, the light inlet surface of the light conductor cable 50 is opposite the light-emitting surface 72 of the light diode 71 and the opening 74 in the light diode 71 at a (small, in particular) distance. Alternatively, the light inlet surface of the light conductor cable 50 is directly contiguous with the light-emitting surface 72 of the light diode 71 or is cemented to it.

Figure 9:
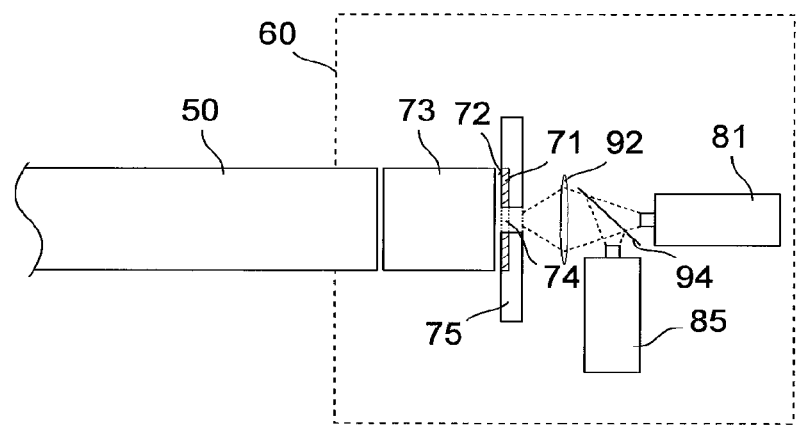
FIG. 9 shows a schematic view of an additional light source device.

FIG. 9 shows a schematic depiction of a light source device 60 that is similar in several characteristics to the light source device presented above with reference to FIG. 8. The light source device 60 is distinguished from the light source device presented above with reference to FIG. 8 in particular in that a second laser diode 85 and a mirror 94 are provided. The second laser diode 85 and the mirror 94 are arranged in such a way that a third light beam generated by the second laser diode 85 is likewise bundled by the object lens 92 into the opening 74 in the light diode 71. Thus, simultaneously or in alternation, the first light beam generated by the light diode 71, the second light beam generated by the first laser diode 81, and the third light beam generated by the second laser diode 85 can be coupled into the illuminating beam path.

The first laser diode 81 and the second laser diode 85 can be configured to emit light of different wavelengths. In this case the mirror 94 in particular is dichroic in order primarily to transmit light of the first laser diode 81 and primarily to reflect light of the second laser diode 85. Possible applications and advantages correspond to those describe above with reference to FIGS. 5 and 6.

Depending on the radiant characteristic of the laser diodes 81, 85, it can be advantageous not to couple the light beams generated by them into lightwave conductors at first, but rather, as shown in FIGS. 8 and 9, to generate an indentation of the light beam or beams generated by the laser diodes 81, 85 in the opening 74 in the light diode 71 by means of a lens or an object lens 92. Contrary to the depiction in FIGS. 8 and 9, however, in each case a lightwave conductor can be additionally provided to transmit the second or third light beam or beams generated by the laser diodes 81, 85 to the lens or object lens 92. In addition, alternatively, the light beams generated by the laser diodes 81, 85 can be combined at first by means of a (in particular dichroic) mirror and then transmitted to the object lens 92 by means of a lightwave conductor. In addition, light beams generated by more than two laser diodes can be brought together by several mirrors, in particular dichroic ones.

Light source devices similar to those shown in FIGS. 8 and 9 can be configured in several openings in the light diode 71 or on one or more sites on the edge of the light diode 71 to generate indentations or narrowings of one or more light beams generated by laser diodes. A coupling of one or more light beams generated by laser diodes in the illuminating beam path on the edge of the light diode 71 can have advantages, which were described above with reference to FIGS. 4 and 6.

Figure 10:
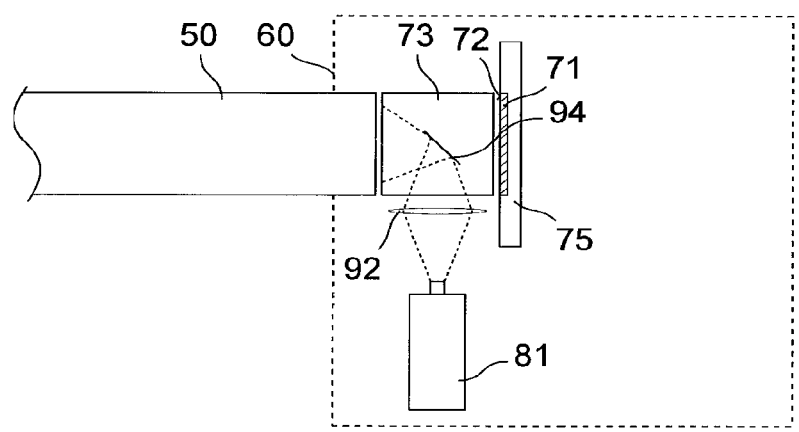
FIG. 10 shows a schematic view of an additional light source device.

FIG. 10 shows a schematic depiction of a light source device 60 that is similar in a few characteristics to the light source devices presented above with reference to FIGS. 2 through 9, in particular to the light source devices presented in connection with FIGS. 4, 7, and 8. Similarly to the light source devices presented above with reference to FIGS. 4 and 7, the light diode 71 has no opening. To couple a second light beam generated by the laser diode 81 into the illuminating beam path, a mirror 94 and, similarly as shown above with reference to FIGS. 8 and 9, an object lens 92 are provided. The mirror 94 is positioned in the light conductor body 73, for example moulded there, and can be dichroic in order primarily to transmit light generated by the light diode 71 and primarily to reflect light generated by the laser diode 81.

The laser diode 81, the object lens 92 and the mirror 94 are positioned in such a way that the second light beam generated by the laser diode 81 runs downstream in the light flux from the mirror 94 or from its reflection on the mirror 94 in the illuminating beam path and essentially parallel to the light beam generated by the light diode 71. Thus the mirror 94 or its reflecting layer constitutes the coupling site. From the coupling site the main radiant direction of the second light beam generated by the laser diode 81 corresponds essentially to the main radiant direction of the first light beam generated by the light diode 71. However, the light beams generated by the light diode 71 and the laser diode 81 can differ from one another also downstream in the light flux from the coupling site in divergence, in intensity distribution over the cross-section of the illuminating beam path, and in other properties.

Contrary to the depiction in FIG. 10, a lightwave conductor can be provided between the laser diode 81 and the lens or object lens 92. In addition, with the help of one or more additional mirrors and/or one or more lenses or object lenses, light beams generated by one or more additional laser diodes can be coupled into the illuminating beam path. Light beams generated by several laser diodes, similarly as presented above with reference to FIG. 9, can be brought together or mixed or coupled separately from one another by several mirrors in the light conductor body 73 before coupling into the illuminating beam path.

The laser diode 81, the object lens 92 and the mirror 94 can be positioned in such a way that the second light beam generated by the laser diode 81 comprises an indentation or narrowing at the coupling site or on the mirror 94. The size or extent of the mirror 94 can be adapted to the cross-section of the second light beam generated by the laser diode 81 at the site of the narrowing. The mirror 94 in this case can be very small, in particular smaller or clearly smaller than a millimeter. In particular if the light diode 71 and the laser diode 81 emit light of the same wavelength, in this manner the shadowing of the first light beam generated by the light diode 71 can be reduced by the mirror 94 to a minimum.

Figure 11:
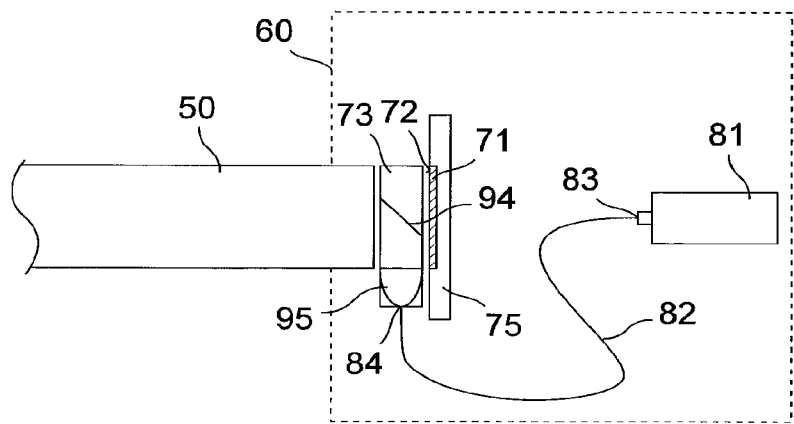
FIG. 11 shows a schematic view of an additional light source device.

FIG. 11 shows a schematic depiction of a light source device 60 that is similar in several characteristics to the light source device presented above with reference to FIG. 10.

Differently from the light source device presented above with reference to FIG. 10, to transmit a second light beam generated by the laser diode 81, a lightwave conductor 82 is provided whose first end 83 is coupled with the laser diode 81. Between the second end 84 of the lightwave conductor 82 and the light conductor body 73 a gradient index lens 95 is positioned to collimate onto the mirror in the light conductor body 73 the second light beam generated by the laser diode 81 and transmitted by means of the lightwave conductor 82. The length of the light conductor body 73 in the longitudinal direction of the illuminating beam path or perpendicular to the light-emitting surface 72 of the light diode 71 is shorter than in the light source device presented above with reference to FIG. 10, but can be equally long. Conversely, also in the light source device presented above with reference to FIG. 10, the light conductor body can be as short as in the light source device 60 from FIG. 11.

Figure 12:
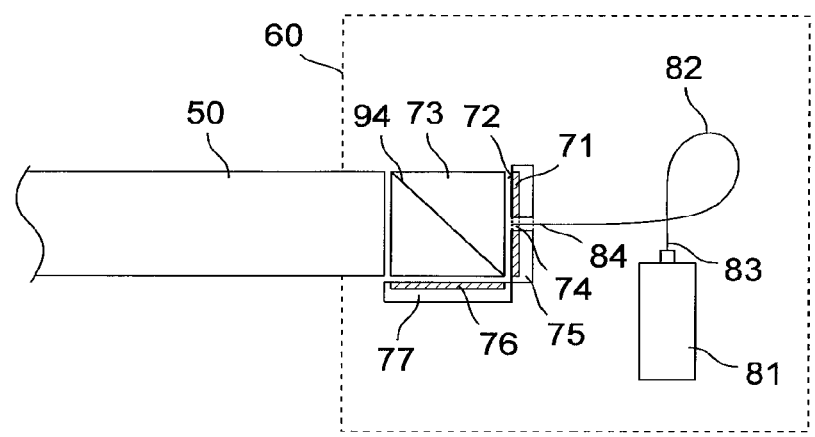
FIG. 12 shows a schematic view of an additional light source device.

FIG. 12 shows a schematic depiction of a light source device 60 that is similar in a few characteristics to the light source device presented above with reference to FIG. 2. A second light diode 76 with a second cooling body 77 is positioned on the light conductor body 73. A mirror 94, which in particular is dichroic, is positioned in the light conductor body 73. The second light diode 76 and the mirror 94 are positioned in such a way that a light beam generated by the second light diode 76 is coupled into the illuminating beam path by means of the mirror 94. Similarly as in the light source devices presented above with reference to FIGS. 10 and 11, the mirror 94 or its reflecting surface thus constitutes the coupling site of the light beam generated by the second light diode 76. From the coupling site or from the mirror 94 downstream in the light flux, the light beam generated by the second light diode 76 runs in the illuminating beam path and essentially parallel to and in the same direction as the light beam generated by the first light diode 71 and the light beam generated by the laser diode 81 and coupled into the illuminating beam path at the second end 84 of the lightwave conductor 82.

For example, one of the two light diodes 71, 76 is a white-light light diode or a white light diode, which is configured to generate light with a spectrum that is perceived as white by the human eye. The respective other light diode is configured, for example, to generate light in the blue or violet spectral range that is suited for exciting fluorescence. The laser diode 81, for example, is likewise configured to emit light suited for exciting fluorescence or to correct or supplement the spectrum generated by the white light diode.

Similarly as mentioned above in reference to other illustrations, the light source device 60 shown in FIG. 2 can also include more than two light diodes and/or several laser diodes 81. To combine or mix the light beams generated by three or more light diodes, two or more mirrors can be provided in the light conductor body 73 and/or outside it, each of said mirrors being in particular dichroic. For example, light diodes can be positioned directly on up to five sides of a square-shaped light conductor body 73. In addition light beams generated by one or more laser diodes, as presented above with reference to FIGS. 2 through 11, can be coupled.

Figure 13:
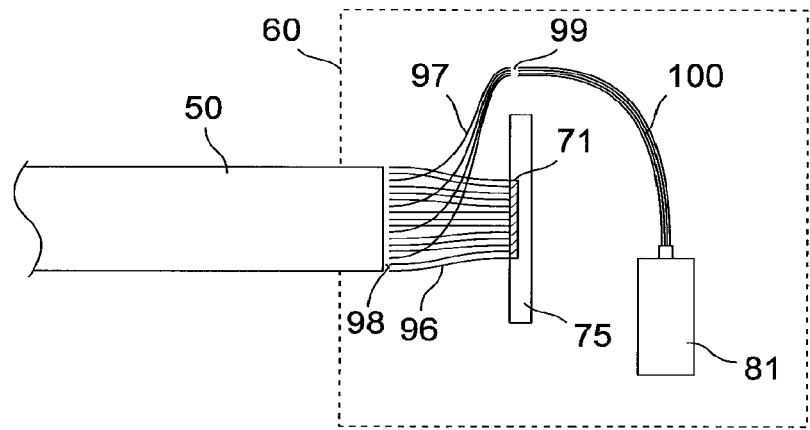
FIG. 13 shows a schematic view of an additional light source device.

FIG. 13 shows a schematic depiction of a light source device 60 with a light diode 71 on a cooling body 75 and a laser diode 81. First lightwave conductors 96 couple the light diode 71 with a light inlet surface of a light conductor cable 50. Second lightwave conductors 97 couple a coupling point 99 with the light inlet surface of the light conductor cable 50. The second ends of the first lightwave conductors 96 and the second ends of the second lightwave conductors 97 are positioned parallel to one another on a surface 98 that is opposite to the light inlet surface of the light conductor cable 50 or identical with it.

One or more third lightwave conductors 100 couple the laser diode 81 with the coupling point 99. The second lightwave conductors 97 and the third lightwave conductor or conductors 100 can be mechanically and optically coupled or connected on the coupling point 99 by means of a plug-in connection or another coupling. For optical coupling a lens, not shown in FIG. 13, or another optical device can be provided optionally. Alternatively, on the coupling site front surfaces of the second lightwave conductors 97 on the one hand and of the third lightwave conductor or conductors 100 on the other hand can directly border on one another. Alternatively, the second lightwave conductors 97, contrary to the depiction in FIG. 13, can be directly connected with the laser diode 81.

The first lightwave conductors 96 or the first lightwave conductors 96 and light conductor cable 50 define an illuminating beam path to provide a first light beam generated by the light diode 71 for an endoscopic or exoscopic application. The second lightwave conductors 97 form a coupling device for coupling the second light beam generated by the laser diode 81 into the illuminating beam path. At the latest from the surface 98, the second light beam generated by the laser diode 81 runs in the illuminating beam path and essentially parallel to the light beam generated by the light diode 71. The coupling site therefore lies on the surface 98 or downstream in the light flux from the same if the second lightwave conductors 97 are already positioned downstream of the light flow of the surface 98 parallel to the first lightwave conductors 96.

The second ends of the first lightwave conductors 96 and the second ends of the second lightwave conductors 97 can each be positioned on the surface 98 randomly, quasi-randomly, or regularly, in particular corresponding to a two- or three-dimensional grid. The second ends of the lightwave conductors 96, 97 can be firmly connected, in particular cemented, with the light inlet surface of the light conductor cable 50. Alternatively the second ends of the lightwave conductors 96, 97 and the surface 98 are opposite to the light inlet surface of the light conductor cable 50 at a distance, or are contiguous with it.

The sum of the individual cross-section surfaces of the light-conducting cores of the second lightwave conductors 97 is smaller than the sum of the individual cross-section surfaces of the light-conducting cores of the first lightwave conductors 96. Therefore the entire cross-section surface of the second light beam generated by the laser diode or diodes 81 is smaller than the entire cross-section surface of the first light beam generated by the light diode 71.

Contrary to FIG. 13, the second light beam generated by the laser diode 81 can be coupled into the illuminating beam path by just one lightwave conductor. Contrary to the depiction in FIG. 13, second light beams generated by more than one light diode 71 and/or by more than one laser diode 81 can be mixed or combined by means of correspondingly positioned lightwave conductors. Contrary to FIG. 13, the first and second lightwave conductors 96, 97 themselves can be conducted further from the coupling site as light conductor cables, for example all the way to a coupling that can be releasably connected with the proximal end 21 of an endoscope 20 as presented above with reference to FIG. 1.

As already mentioned several times, characteristics of the light source devices presented above with reference to FIGS. 2 through 13 can in some cases be combined with one another. In addition, in the light source devices presented above with reference to FIGS. 2 through 13, mirrors can be replaced by grids, in particular when they are foreseen for reflection of essentially monochromatic laser radiance. If, instead of dichroic mirrors, those with reflection that depends on polarization are used, light beams of corresponding polarization, even at equal wavelength, can be combined without loss or without great loss.

As formerly mentioned, in most of the light source devices presented above with reference to FIGS. 2 through 14, instead of one light diode, several light diodes or an array of light diodes can be provided. Light diodes of an array can generate light with the same spectra or with different spectra. Light diodes can be replaced by other light sources, in particular flat ones. Laser diodes can be replaced by other lasers or by other light sources. For example, laser diodes can be replaced by light diodes that are combined with a photonic grid or comprise a photonic grid.

Contrary to the previous presentations with reference to FIGS. 1 through 13, the light source devices can be provided not as separate units or apparatuses, but rather can be partly or completely integrated in an endoscope or exoscope.

Figure 14:
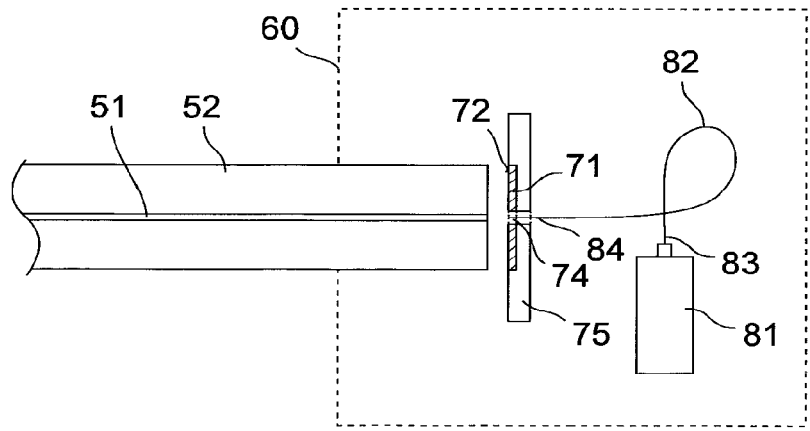
FIG. 14 shows a schematic view of an additional light source device.

FIG. 14 shows a schematic depiction of a light source device 60 that is similar in a few characteristics to the light source devices presented above with reference to FIG. 3. Unlike in the light source devices presented above with reference to FIG. 3, a coaxial arrangement is foreseen consisting of an inner lightwave conductor 51 and an outer lightwave conductor 52. The inner lightwave conductor 51 has a smaller cross-section and is positioned opposite the opening 74 in the light diode 71. The outer lightwave conductor 52 has a ring-shaped cross-section, which corresponds at least approximately to the light-emitting surface 72 of the light diode 71 and is positioned opposite to it.

An intermediate space is provided between the light-emitting surface 72 of the light diode 71 and the light inlet surface of the coaxial arrangement of the inner lightwave conductor 51 and the outer lightwave conductor 52. This intermediate space forms a common illuminating beam path, in which the light beam generated by the light diode 71 and light beam generated by the laser diode 81 partly mix with one another.

Figure 15:
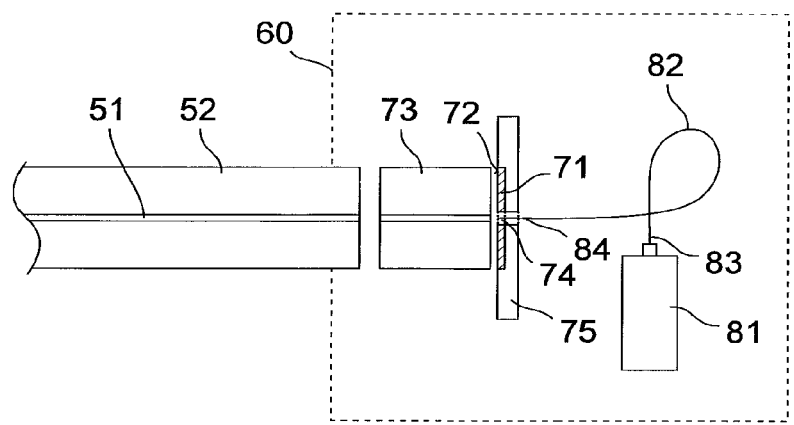
FIG. 15 shows a schematic view of an additional light source device.

FIG. 15 shows a schematic depiction of a light source device 60 that is similar in a few characteristics to the light source devices presented above with reference to FIGS. 3 and 14. Contrary to the light source device presented above and in FIG. 14, a light conductor body 73 is provided between the light diode 71 and the second end 84 of the lightwave conductor 82 on the one hand and between the light inlet surface of the coaxial arrangement of the inner lightwave conductor 51 and the outer lightwave conductor 52 on the other hand. The light conductor body 73, however, unlike in the examples presented above with reference to FIGS. 2 and 4 through 9 for instance, has a cross-section that corresponds at least essentially to the cross-section of the coaxial arrangement of the inner lightwave conductor 51 and of the outer lightwave conductor 52.

An intermediate space is provided at least either between the light-emitting surface 72 of the light source 71 and the light inlet surface of the light conductor body 73 or between the light outlet surface of the light conductor body 73 and the light inlet surface of the coaxial arrangement of the inner lightwave conductor 51 and the outer lightwave conductor 52. This intermediate space forms a common illuminating beam path, in which the light beam generated by the light diode 71 and the light beam generated by the laser diode 81 mix to some extent. Alternatively, in the light source devices presented in FIGS. 14 and 15, the intermediate space can be dispensed with.

Figure 16:
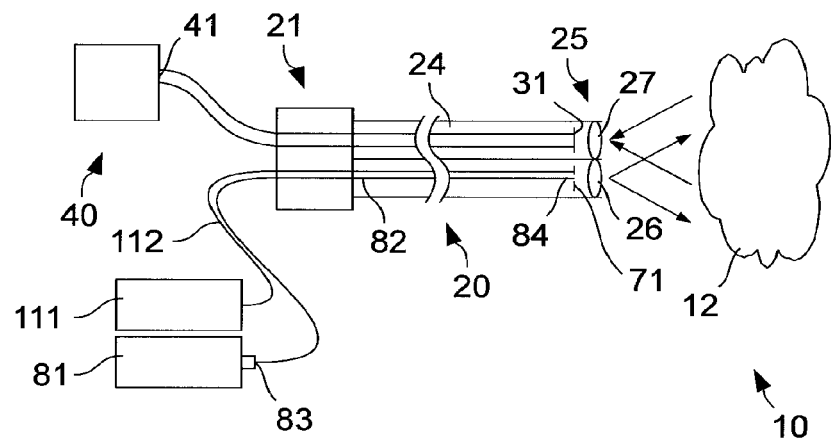
FIG. 16 shows a schematic view of an endoscope.

FIG. 16 shows a schematic depiction of an example of an endoscopy system 10 with an endoscope 10 that is similar in a few characteristics to the endoscope presented above with reference to FIG. 1. Unlike in the endoscopy system presented above and in FIG. 1, a light diode 71 is positioned on the distal end 25 of the endoscope 20. A laser diode 81, which is positioned outside the endoscope 20, is coupled with the distal end 25 of the endoscope 20 by a lightwave conductor 82. A first end 83 of the lightwave conductor 82 is coupled with the laser diode 81, and a second end 84 of the lightwave conductor 82 is positioned in an opening in the light diode 71.

A power supply device 111 is connected with the first light diode 71 on the distal end 25 of the endoscope 20 by a power supply line 112. The power supply device 111 is provided to supply the light diode 71 with electric current. In addition the power supply device 111 can be provided for power supply of the laser diode 81. The power supply device 111 and the laser diode 81 can be integrated in an apparatus or in a unit. The lightwave conductor 82 and the power supply line 112 can be integrated in a cable, at least between the laser diode 81, the power supply device 111 or an apparatus that integrates both on the one hand and the endoscope 20 on the other hand. Plug-in connections or other couplings can be provided on the laser diode 81, the power supply device 111 and/or the endoscope 20 so that they can be separated from the lightwave conductor 82, the power supply line 112 or the cable that integrates both.

The area on the distal end 25 of the endoscope 20 downstream in the light flux from the light diode 71 as far as the light outlet window 26 and including it, forms an illuminating beam path to provide illuminating light to illuminate the object 12. The light outlet surface on the second end 84 of the lightwave conductor 82 forms the coupling site from which, downstream in the light flux, the second light beam generated by the laser diode 81 and transmitted by the lightwave conductor is coupled into the illuminating beam path. The second light beam generated by the laser diode 81 runs in the illuminating beam path from the coupling site and essentially parallel to the first light beam generated by the light diode 71.

Contrary to the depiction in FIG. 14, numerous light source devices presented above with reference to FIGS. 2 through 13 can be integrated partly or completely into an endoscope. Thus the light diodes and/or the laser diodes can each be positioned on the distal end 25 or on the proximal end 21 of the endoscope 20. In particular by means of the lightwave conductors 82, 97 described above with reference to FIGS. 2 through 7 and FIGS. 11 through 13, light beams generated by laser diodes spatially distanced from one another can be coupled into the illuminating beam path.

Figure 17:
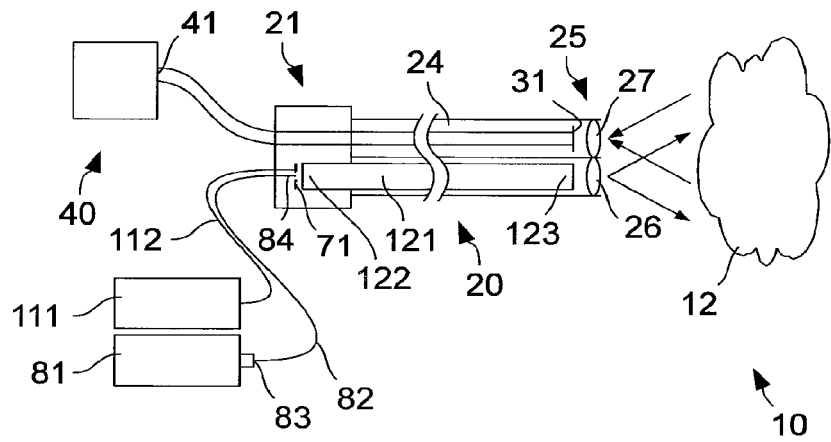
FIG. 17 shows a schematic view of an additional endoscope.

FIG. 17 shows a schematic depiction of an additional example of an endoscopy system 10, which is similar to the endoscopy system presented above with reference to FIG. 16. Contrary to the endoscopy system presented above with reference to FIG. 16, in the endoscopy system 10 shown in FIG. 17 the light diode 71 is not positioned on the distal end 25 but on the proximal end 21 of the endoscope 20. Similarly to the endoscopy system presented above and in FIG. 16, however, here too a second end 84 of the lightwave conductor 82 is positioned in an opening in the light diode 71.

An additional lightwave conductor 121 is positioned in the shaft 24 of the endoscope 20. A first, proximal end 122 of the additional lightwave conductor 121 is positioned on the proximal end 21 of the endoscope opposite the light diode 71 and the second end 84 of the lightwave conductor 82 or bordering on these or is permanently connected with them, for example by cementing. A second, distal end 123 of the additional lightwave conductor 121 is positioned on the distal end 25 of the endoscope 20 on the light outlet window 26. The light beam generated by the light diode 71 and the light wave generated by the laser diode 81 are together transmitted by the other lightwave conductor 121 from the proximal end 21 to the distal end 25 of the endoscope 20, where they exit together through the light outlet window 26.

In both of the endoscopy systems presented above with reference to FIGS. 16 and 17, the proximal end 21 of the endoscope 20 can be connected with an apparatus or a unit that integrates the laser diode 81 and the power supply 111, by means of a cable in which the lightwave conductor 82 and the power supply line 112 are integrated. The lightwave conductor 82 and thus also the cable can be especially thin and flexible.

What is claimed is:

1. An endoscopy or exoscopy system comprising:
    an endoscope or exoscope;
    a light source comprising:
        a flat first light source;
        a second light source;
        an illuminating beam path that is configured to provide a first light beam emanating from the first light source; and
    a coupling device including a lightwave conductor or lens system for coupling a second light beam from the second light source into the illuminating beam path,
    wherein the coupling device the second light beam from the second light source is positioned near, in or before the light emitting surface of the first light source.

2. The system of claim 1, wherein a cross-section surface of the second light beam is not more than half of a cross-section surface of the first light beam.

3. The system of claim 1, wherein the first light source includes a semiconductor light source with an array of light diodes or an array of other light-emitting elements and the coupling site is positioned between light diodes or other light-emitting elements of the array.

4. The system of claim 1, wherein the first light source includes a light diode with an opening, so that the coupling site is positioned at the opening.

5. The system of claim 1, wherein the lens system of the coupling device includes at least either an object lens, a curved mirror, an optical grid or an imaging device that reduces a cross-section of the second light beam.

6. The system of claim 5, wherein the imaging device is configured and positioned to produce an indentation of the second light beam on the edge of the light-emitting surface of the first light source, in an opening in the light-emitting surface of the first light source or in the illuminating beam path before the light-emitting surface of the first light source.

7. The system of claim 1, wherein the coupling device includes a deflection mirror that is positioned in the illuminating beam path before the light-emitting surface of the first light source.

8. The system of claim 7, wherein the imaging device generates the indentation of the second light beam at or close to the site of the deflection mirror.

9. The system of claim 7, wherein the deflection mirror is embedded in a light conductor body.

10. The system of claim 7, wherein
    the coupling device includes several second lightwave conductors,
    the second ends of the first lightwave conductors and the second ends of the second lightwave conductors are positioned in the surface randomly or quasi-randomly or regularly distributed.

11. The system of claim 1, wherein the second light source includes a laser diode, another diode laser, or another laser.

12. The system of claim 1, wherein the first light source is positioned in the endoscope or in an exoscope and the second light source is positioned separate from the endoscope or exoscope.

13. The system of claim 1, wherein the lightwave conductor has a first end and a second end, where the first end of the lightwave conductor is coupled with the second light source, and where the second end of the lightwave conductor is positioned near, in or before the light-emitting surface of the first light source.

14. The system of claim 1, where the coupling device is configured in such a way that at the coupling site the cross-section surface of the second light beam is smaller than the cross-section surface of the first light beam.

15. A light source coupled to an endoscope or to an exoscope, the light source device comprising:
    a housing;
    a flat first light source located within the house;
    a second light source located within the housing;
    an illuminating beam path that is configured to provide a first light beam emanating from the first light source;
    a coupling device for coupling a second light beam from the second light source into the illuminating beam path,
    wherein the illuminating beam path includes several first lightwave conductors whose first ends are coupled with the first light source,
    wherein the coupling device includes at least one second lightwave conductor whose first end is coupled with the second light source, and
    wherein second ends of the first lightwave conductor and of the at least one second lightwave conductor are positioned parallel and close to one another, forming a surface.

16. A light source device coupled to an endoscope or an exoscope, the light source device comprising:
    a housing;
    a flat first light source located within the housing;
    a second light source located within the housing;
    an illuminating beam path that is configured to provide a first light beam emanating from the first light source;
    a coupling device including a lightwave conductor or a lens system for coupling a second light beam from the second light source into the illuminating beam path,
    wherein the first light source is configured to generate a first spectrum with a first half-width, and wherein the second light source is configured to generate a second spectrum with a second half-width, so that the second half-width is no more than half of the first half-width.

* * * * *